United States Patent [19]

Cziffer et al.

[11] Patent Number: 4,969,886
[45] Date of Patent: Nov. 13, 1990

[54] DISPOSABLE FIXING MEANS ESPECIALLY FOR FIXING FACTURED SMALL TUBULAR BONES EXTERNALLY

[76] Inventors: Endre Cziffer, Bakats u. 5, II.em.5; Mihaly Szacsky, Varosmajor u. 26/b; Tibor Bagits, Lekai János tér 15, all of Budapest, Hungary

[21] Appl. No.: 273,862
[22] PCT Filed: Sep. 15, 1987
[86] PCT No.: PCT/HU87/00038
  § 371 Date: Nov. 23, 1988
  § 102(e) Date: Nov. 23, 1988
[87] PCT Pub. No.: WO88/05288
  PCT Pub. Date: Jul. 28, 1988

[30] Foreign Application Priority Data

Jan. 23, 1987 [HU] Hungary .............................. 206/87

[51] Int. Cl.⁵ .................................................. A61F 5/04
[52] U.S. Cl. ........................................ 606/59; 606/69; 606/78
[58] Field of Search ................. 128/87 A, 87 R, 89 R, 128/92 Z, 92 ZK, 92 ZY; 606/54, 59, 60, 61, 69, 70, 71, 72, 75, 78

[56] References Cited

U.S. PATENT DOCUMENTS

| | | | |
|---|---|---|---|
| 3,943,923 | 3/1976 | Scheinberg | 128/89 R |
| 4,360,012 | 11/1982 | McHarrie et al. | |
| 4,628,919 | 12/1986 | Clyburn | |
| 4,628,921 | 12/1986 | Rousso | 128/92 Z |
| 4,696,293 | 9/1987 | Ciullo | 128/92 ZK |

Primary Examiner—Robert A. Hafer
Assistant Examiner—Lynda M. Cofsky
Attorney, Agent, or Firm—Herbert Dubno

[57] ABSTRACT

A disposable fixing device serving for an external fixation of fractured small tubular bones includes rods having a generally circular cross-section and at least one flattened face and provided with a plurality of bores spaced apart and traversing the rod through the entire width thereof and a plurality of pins introduced into the fractured bone by one end thereof and connected with the respective bores of the rod by an opposite end upon sealing each of the pins to the opposite sides of the respective rod.

5 Claims, 4 Drawing Sheets

DISPOSABLE FIXING MEANS ESPECIALLY FOR FIXING FACTURED SMALL TUBULAR BONES EXTERNALLY

CROSS REFERENCE TO RELATED APPLICATIONS

This application is a national phase application of PCT/HU87/00038 filed 15 Sept. 1987 and based, in turn, upon Hungarian national application 206/87 filed 23 Jan. 1987 under the International Convention.

FIELD OF THE INVENTION

Our present invention relates to a disposable fixator mainly for fixing fractured small tubular bones, as well as to a method of using the fixator.

BACKGROUND OF THE INVENTION

The availability of external fixing means fixator has opened new fields in surgery. Fixators must meet requirements for quick accurate and perfect applicability. In the case of repositioning and stable fixing of fractured small tubular bones, in particular with open fractures accompanied by injuries to bones and soft tissues, it is of utmost importance that functional ability of the body part due to lack of motion shouldn't weaken it.

In the special literature and practice J. Kearney Rogers reported in 1827 for the first time on the application of the so-called 37 bone structure". In 1853 Malgaigne was the first to use an external fixator. Berenger and Faraud were the first to use bone structure and an external fixing wooden frame. In 1894 Clayton Parkhill proposed for the first time the use of an outer fixator made of metal.

In this century, Roger Anderson applied external fixators with connecting rods assembled of pins and plaster. Generally applicable external fixators were developed by Haynes. Judet 1934, 1959) dealt with the extension of compression possibilities. Elisarev and Gudusauri (in 1972) bered through the bones with the so-called Kirschner wires, the ends of which were provided with special tensioning circular frame.

A method for external fixing of the AO-Company—Arbeitsgemein— schaft fur Osteoxynthesefragen— was described by Bandi in 1972, then Holz and Weller in 1975. The term "osteotaxis" is linked with Hoffmann (1959), and the method was developed by Vidal (1960, 1967) who combined the advantage of the different methods.

In World War II the apparatus of Hoffmann and Haynes was widely used. Finally Waknitz developed the so-called mini fixing means.

Presently the most widely used type are the distraction devices of Kessler, Roger Anderson, Synthes Tower and Matev. External fixing means of the Hoffmann type is also known. Recently a new type of fixator referred to as the Jaquet assembly has been proposed. In Hungary the external mini fixing means of the Hoffmann type produced by the Swiss Company Jaquet Freres are mostly used.

In course of application of the presently used widespread types of fixators for the pins, skilled work requiring high professional skills must be performed. After having fitted the bones with utmost accuracy, it is expedient to fix the ideal position in the simplest possible way. However, after reposition the injured surface must be left free to enable attention of the wound. One of the methods is the so-called cement-pin-fixation, requiring the most accurate applying of cement. For the phase of applying the cement, the proper position must be maintained. When the cement has hardened, correction becomes possible only by destroying the cement.

The external mini fixing means of Jaquet, having been developed expressly for treating the injuries of small tubular bones, can be easily manipulated by comparison of other known types of fixators. However, modelability in every direction and easy reposition requires complex equipment consisting of pliers, wrenches, guiding devices, screws, spikes, clamping means, cardan shafts, and industrial boring drills. This equipment is expensive. The fixators are made of chrome steel and generally are intended for repeated use.

Considering that a number of elements to be used in course of a surgical intervention cannot be predetermined, the whole assembly has to be at the disposal of the surgeon. Accurate adjustment of the clamping means and links requires several professional tricks. As the size of the connecting stiffening rods is given, the angles of deviations are corrected by applying a slope. The mini fixing means of the Jaquet-type has to be built-up of several components on the fixed body-part, even in the simplest cases. In case of possible change of position screwed connections have to be released and the fixing means have to be arranged in a new position.

As already mentioned, an adequate quantity of the components of the Jaquet mini-fixators has to be kept of store, as the quantity and quality of the elements to be assembled are always changing.

The patient provided with the fixator can be an outpatient, who can depart with the expensive equipment, especially if he can remove it, thus delaying the healing process. Additionally, the most expensive elements cannot be repeatedly used if they do not return to the hospital at all. Because of such permanent use, the terms of reusability of the fixators are variable. Replacement of fixators which have become lost or damaged is difficult.

OBJECTS OF THE INVENTION

An object of the present invention is to eliminate the deficiencies of known external fixing means. Another object of the present invention is to provide a disposable fixator, which is inexpensive, easy to manipulate and can assure perfect fixation so that in its use surgical techniques become simpler and quicker.

SUMMARY OF THE INVENTION

The present invention is based on the recognition that initial plasticity as is the case with fixing with cement and advantageous characteristics of the mini fixing means of Jaquet type can be united by using fixing rods made of an easily processable and flexible soft metal.

According to the invention, the external fixator is formed as a non-reusable disposable device, which can be easily bent to the desired shape and in the form of a rod of a soft metal, preferably aluminum, in which equally spaced bores are formed and standardized pins or the so-called Kirschner wires known per se can be inserted into the bores with parallel axes.

The fixing rods made of the soft metal have advantageously a circular cross-section.

On the fixing rods, a flat surface can be formed parallel with the longitudinal axis of the rod and perpendicular to the axis of the bores at one or both ends of the bores. The fixator rods of the present invention are prefabricated in a length complying with practical requirements, optionally pre-sterilized and packed as separated components or in a set or kit.

The fixing rods can be formed as compressor-distractors also. At the ends of two halves of a rod a right-handed and a left-handed thread are formed, respectively. The threaded ends are screwed into a rotating part provided with a bore with right-handed and left-handed threads at the ends. By rotating the rotating part in one direction, the two pieces of the fixing rod are pulled toward each other while, by rotating the rotating part in the other direction, they are removed from each other. In the former case the fixator acts as a compressor. In the latter case the fixator acts as a distractor; that means, that alternatively compression and distraction can be performed.

The disposable fixing are positioned in the following manner:

The fixing rod made of soft metal is cut to the necessary length by using pliers.

Thereafter the fixing rod is bent into a shape corresponding to the form of the injured or fractured part of the body. The pins which have been previously introduced into the bone are led through the bores of the fixing rod. Alternatively, the pins are introduced into the bone through the bores of the fixing rod. In the regions of the bores receiving the pins, the fixing rod is compressed onto the pins by using well known crimping pliers, whereby a difficulty releasable bond is obtained between the pins and the fixing rod. If necessary, the fixator is finally positioned by means of a bending-modelling device, e.g. pliers serving for this purpose.

With the fixator according to the present invention spaces between the bores in the fixing rods make the use of a boring gauge—the so-called predrilling guide—superfluous. It goes without saying that both the diameter of the bores and spaces between them should be chosen in accordance with the sizes of the pins and practicability; diverse sizes are possible.

Linkages and clamping means common with earlier fixators of the known types thus become superfluous.

Fixed bend, arcuate sections can be modified optionally without losing their stability.

The first pliers used are needed for cutting the fixing rods to the necessary length. However, these pliers are well suited also for cutting the Kirschner wires to size, nipping off, and for cutting off from the fixing rod.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
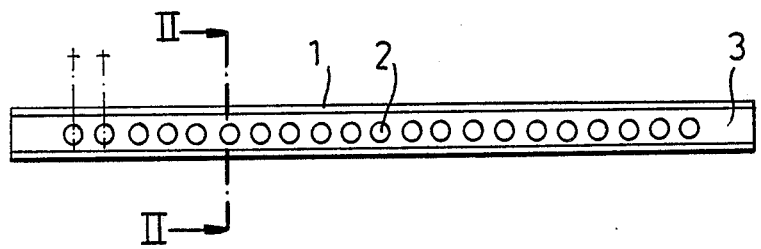
FIG. 1 is a schematic front view of the fixing rod.
Figure 2:
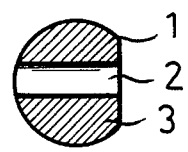
FIG. 2 is a sectional view taken along the line II—II of FIG.
Figure 2A:
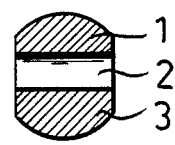
FIG. 2A is a view similar to FIG. 2 showing an embodiment in which two flat surfaces are provided.

Fixing rod 1 as shown in FIGS. 1 and 2 is made of an easily bendable flexible soft metal, especially of aluminum. It has a circular cross section and contains evenly spaced bores 2 with axes parallel to each other. From FIG. 2 it will be apparent that the cross section of the fixing rod 1 is not absolutely circular but has a flat surface 3 perpendicular to the axes of the bores and parallel to the axis of the fixing rod 1. The fixing rod 1 can be formed also so that at both ends of the bores 2 a respective flat surface 3 is formed.

Figure 3:
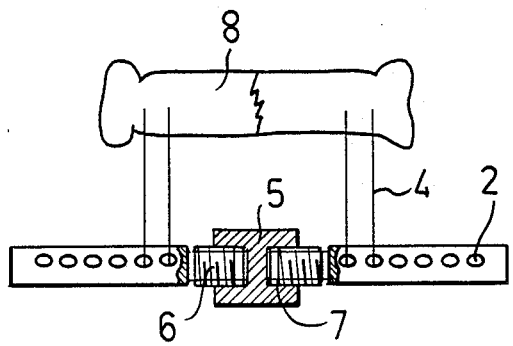
FIG. 3 is an elevational view, partly broken away, which illustrates the scheme of the version of the fixing rod assembled of two pieces used as a compressor or distractor in course of use.

In FIG. 3 an embodiment is to be seen with which the fixing rod is assembled of two separate pieces. At the ends facing each other threaded parts are formed, namely with a right-handed thread on one end and a left-handed thread on the other end. The threaded parts 6 are screwed into the bores 7 also formed with a right-handed and left-handed thread, respectively, of a rotating part 5 inserted therebetween. In FIG. 3, it can be seen that the pins 4, having been introduced into the injured fractured bone 8, are led through the bores 2 in the fixing rods 1.

Figure 4:
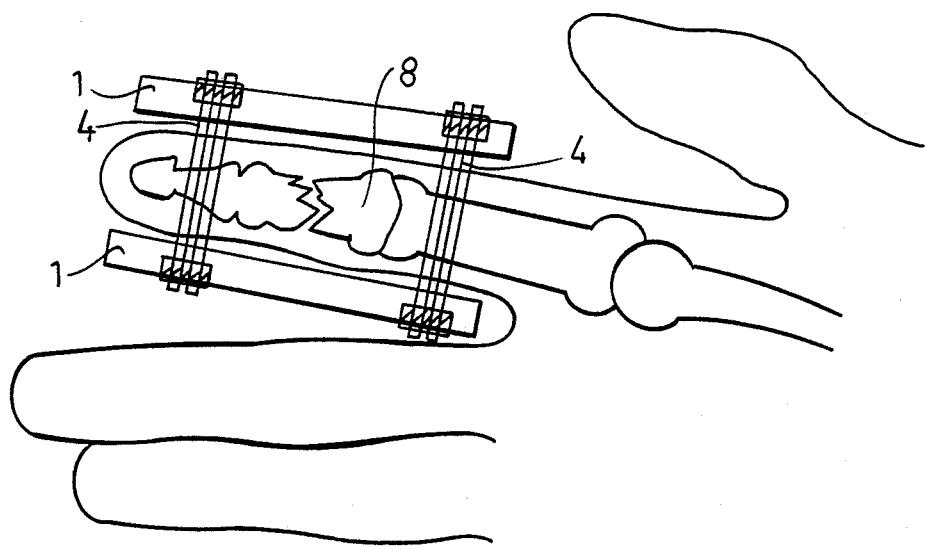
FIG. 4 is a diagram which shows the means according to the invention as positioned on a finger.

Further FIGURES show the diverse modes of application of the means according to the invention. FIG. 4 shown schematically the fixing means as positioned on the long finger. A fractured bone is indicated by the reference numeral 8 in this case too.

Figure 5:
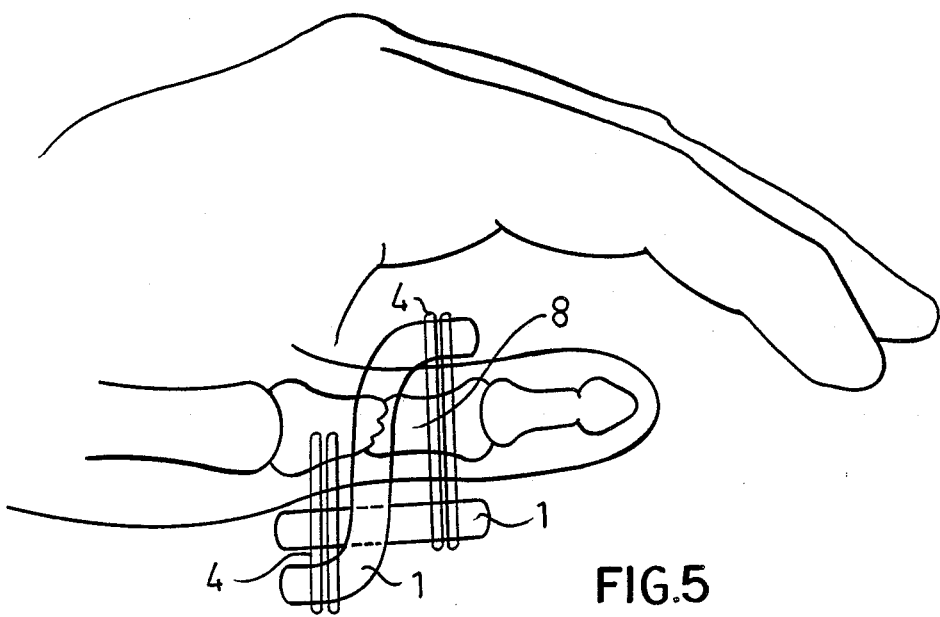
FIG. 5 is another diagram which illustrates the means according to the invention applied on the thumb.
Figure 6:
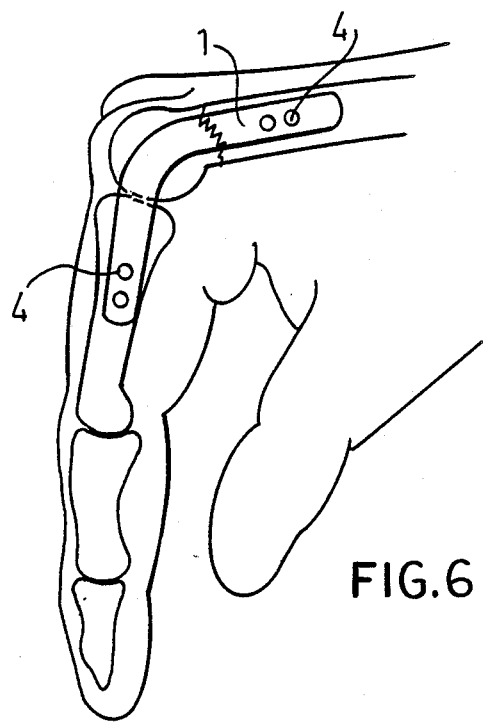
FIG. 6 is yet another diagram which shows a further mode of application, namely for fixing a fracture of the metacarpal bone of the hand subcapital.
Figure 7:
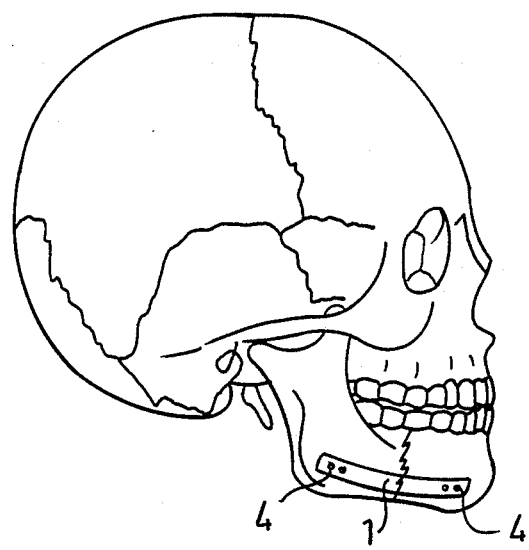
FIG. 7 is a diagram which shows the device positioned on a fracture of the jaw.

FIG. 5 illustrates the mode of application on a thumb. From FIG. 6 is will be obvious that the device can fix a fracture of the metacarpal bone of the hand subcapital. In FIG. 6 the joint is closed in the functional position. FIG. 7 illustrates the possibility of positioning the device on a fractured jaw.

Figure 8:
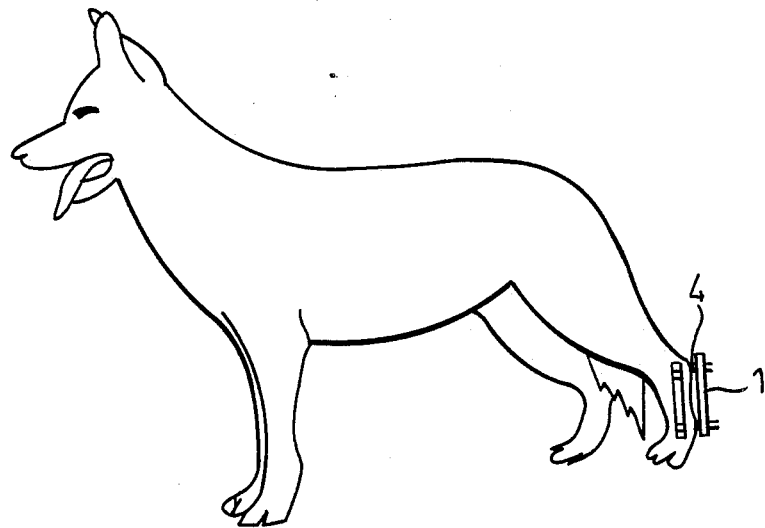
FIG. 8 is a diagram which illustrates a possibility of application of the invention in veterinary surgery.
Figure 9:
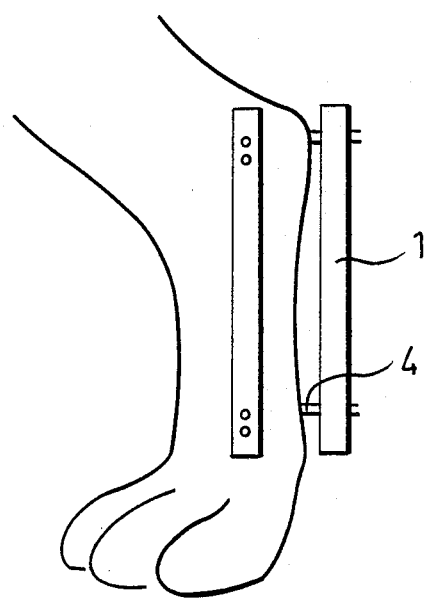
FIG. 9 shows a detail of FIG. 8 in an enlarged scale.

Firstly, in FIG. 8 we have shown an example of the device in veterinary surgery. FIG. 9 shows the relevant part of FIG. 8 to an enlarged scale.

The disposable fixing means according to the present invention can be preferably used in a catastrophe situation and under field conditions. Fixators can be pre-sterilized and packed, accordingly; local sterilization is not required. Corrections taking place in course of positioning the pin by using a hand-drill can be properly made because of the plasticity of the fixing rods formed in compliance with the invention.

External fixing means applied under field circumstances need not be removed when the patient is attended in the hospital as in sense of the invention necessary corrections can be performed by means of the third pliers, i.e. with the pins and Kirschner wires left in. Fixing rods may be removed and replaced. This possibility allows observation of wounds to a considerable extent. Following final positioning continuous observation becomes possible, occurrence of infection can be immediately seen.

Because of the light weight of the fixator according to the invention, mobility of the patient is not at all disturbed. Sealing established by connecting Kirschner wires and fixators prevents noncompetent undoing of the bond. Closing of the bond is assured by using the aforementioned sealing pliers.

One of the most important advantages of the invention is that the whole set can be transported in a set-storing unit. The set consists of three pliers, differently dimensioned fixing rods and pins and the Kirschner wires. In a practical embodiment the fixing rods can be interchangeable, as in a magazine.

The fixing rods 1 can be made of soft aluminum with a 6 mm diameter having at one side thereof a flattened planar surface 3. The bores 2 running perpendicularly to the flat surface 3 are formed with a diameter of 1.5 and 2 mm. They are arranged with a 3 mm space in between. Fixing rods 1 are prepared expendiently in lengths of 100 or 200 mm. In the course of surgical attention, the fixing rod 1 can be formed according to necessity and cut to size by means of commercially available pliers. Fixing rods 1 made of aluminum can be bent up to an angle of 90° with the proper radius and bent with a curvature radius of 4 to 5 cm in compliance with prevailing requirements. Accordingly, the means according to the invention can be modelled in every direction. The material of the fixing rod 1 makes it possible for the operating surgeon to adjust the position of the fixing by hand. After having introduced the pins 4 or Kirschner wires through the bores 2, these are fixed by the so-called sealing pliers, by applying pressure onto the region of the bore 2 receiving the pin 4 from both sides. Meanwhile the material of the rod 1 is compacted and slightly hardened. As a consequence strength is also increased. After having performed fixing and sealing, by using the third pliers positioning according to need is effected. For the sake of observation of the wound, radial parts can be formed on the fixing rod 1, not at all reducing stability of the fixator. On the contrary, stability will be increased. With the fixator means according to the invention, the position of the treated finger cannot be changed by its own muscular strength.

The fixing means according to the invention contains neither clamping means nor linkages. It fits plastically to the injured part of the body. As a consequence, the patient can tolerate the duration of healing more easily.

Fixing means according to the invention are well suitable for fixing both in parallel and transverse directions. Combined positioning guarantees extra stability. By radial bending with the third pliers, a so-called "vaulted" fixation can also be obtained.

Summing up what has been said, the fixing means according to the invention can be well used for the restoration and fixing of traumatic deviations of all small bones, in particular in hand surgery. So, for example, it can be used for fresh injuries penetrating into the open joint, fresh open transverse fractures, communication, reposition of obtuse crushing fractures, injuries resulting from shooting, and for the attention of infected wounds and fractures. Furthermore, the fixing means are well suitable for the external fixation of small tubular bones of the feet, for fixing fractured jaws, in the therapy of newborn babies, pediatrical surgery, and small animal therapy (dogs, cats, etc.) for reposition and fixing of fractured extremities. Applicability is enabled by the multi-dimensional adjustability.

Operations of the aforementioned character can be practically performed even under minimally acceptable circumstances. In comparison to presently applied techniques. The duration of operation can be considerably shortened.

As already detailed, fixing means according to the invention differ considerably from known solutions in respect to technical design and advantages resulting therefrom. Application increases significantly the general use of surgical techniques to be realized with external fixation. Even departments, (wards in hospitals) can use the external fixing means according to fixators up to now. The fixator improves considerably quickness and accuracy in the operation.

As an unexpected and surprising advantage one can mention the possibility of ad hoc application (catastrophe, war, etc.) as well as the fact that due to its inexpensiveness and simplicity it can become expendable in therapy; that means that the fixator can be brought to the market as disposable devices.

We claim:
1. An apparatus for spanning a fracture for fixing bones, comprising:
   a soft metal elongated flexible rod having a longitudinal axis freely bendable over its entire length, said rod having a generally circular cross-section and being formed with at least one elongated continuous flattened face parallel to said axis and extending substantially over an entire length of said rod;
   a plurality of equidistantly spaced apart bores formed in said rod opening at said flattened face and extending through said rod perpendicular to said axis; and
   a plurality of pins passing through respective ones of said bores, penetrating said bores and extending generally perpendicular to said flattened face of said rod, said pins being held in said rod by squeezed in portions of the rod in the region of said bores.

2. The apparatus defined in claim 1 wherein said rod had a further flattened face spaced from and parallel to the first-mentioned elongated flattened face and perpendicular to said bores.

3. The apparatus defined in claim 1 wherein said pins are KIRSCHNER pins.

4. The apparatus defined in claim 1 wherein said rod is made out of aluminum.

5. The apparatus defined in claim 1, further comprising:
   another flexible rod identical to and coaxial with the first-mentioned flexible rod, each of said flexible rods being formed with a respective threaded end with a respective threaded element screwed into the respective end of the respective rod, said threaded ends of said rods being spaced apart and facing each other, and
   a rotating element formed with opposite sides each rotatably connected with the respective end of said rods screwed with the respective threaded element, so that said rods can be axially shifted toward and away from one another.

* * * * *